(12) United States Patent
Weichselbaum

(10) Patent No.: US 9,958,384 B2
(45) Date of Patent: *May 1, 2018

(54) METHOD OF DETECTING BACTERIA IN A FLUID USING FORWARD-SCATTER TECHNIQUE

(71) Applicant: BacterioScan LTD., MP Western Galilee (IL)

(72) Inventor: Amnon Weichselbaum, Haifa (IL)

(73) Assignee: BacterioScan LTD., MP Western Galilee (IL)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/183,969

(22) Filed: Jun. 16, 2016

(65) Prior Publication Data

US 2016/0299067 A1 Oct. 13, 2016

Related U.S. Application Data

(60) Continuation of application No. 14/577,750, filed on Dec. 19, 2014, now Pat. No. 9,395,297, which is a (Continued)

(30) Foreign Application Priority Data

Aug. 8, 2006 (GB) .................................. 0615692.1

(51) Int. Cl.
*G01N 21/51* (2006.01)
*C12Q 1/04* (2006.01)
(Continued)

(52) U.S. Cl.
CPC ................ *G01N 21/51* (2013.01); *B01L 3/50* (2013.01); *B01L 3/508* (2013.01); *C12Q 1/04* (2013.01);
(Continued)

(58) Field of Classification Search
CPC ........ G01N 21/49; G01N 21/03; G01N 21/51; G01N 33/493; G01N 2015/0693;
(Continued)

(56) References Cited

U.S. PATENT DOCUMENTS 3,627,424 A 12/1971 Dorman et al.
3,832,532 A 8/1974 Praglin et al.
(Continued)

FOREIGN PATENT DOCUMENTS

DE 10128978 12/2002
EP 0320154 6/1989
(Continued)

OTHER PUBLICATIONS

Murray, et al. "Light-scattering methods for antibiotic sensitivity tests", J Clin Pathol, 1980, vol. 33, pp. 995-1001, 8 pages.
(Continued)

*Primary Examiner* — Michael P LaPage
(74) *Attorney, Agent, or Firm* — Nixon Peabody LLP

(57) ABSTRACT

A method for detecting and counting particles suspended in fluids, such as bacteria suspended in urine, utilizing dynamic features of the suspended particles and employing light scattering measurements. The disclosed method is suitable for determining the susceptibility of bacteria to antibiotics. A cuvette for detecting bacteria in fluids, which is especially suited for the light scattering measurements, is provided.

14 Claims, 7 Drawing Sheets

Related U.S. Application Data continuation of application No. 13/689,000, filed on Nov. 29, 2012, now abandoned, which is a division of application No. 12/085,708, filed as application No. PCT/IL2006/001379 on Nov. 29, 2006, now Pat. No. 8,339,601.

(60) Provisional application No. 60/597,395, filed on Nov. 29, 2005.

(51) Int. Cl.

| | | |
|---|---|---|
| *C12Q 1/06* | (2006.01) | |
| *C12Q 1/18* | (2006.01) | |
| *G01N 21/03* | (2006.01) | |
| *G01N 33/493* | (2006.01) | |
| *B01L 3/00* | (2006.01) | |
| *G01N 21/49* | (2006.01) | |
| *G01N 33/487* | (2006.01) | |
| *C12Q 1/10* | (2006.01) | |
| *G01N 15/06* | (2006.01) | |

(52) U.S. Cl.
CPC .............. *C12Q 1/06* (2013.01); *C12Q 1/10* (2013.01); *C12Q 1/18* (2013.01); *G01N 21/03* (2013.01); *G01N 21/49* (2013.01); *G01N 33/4875* (2013.01); *G01N 33/493* (2013.01); *B01L 2300/04* (2013.01); *B01L 2300/0809* (2013.01); *G01N 2015/0693* (2013.01); *G01N 2021/0346* (2013.01); *G01N 2021/0389* (2013.01); *G01N 2021/513* (2013.01)

(58) Field of Classification Search
CPC ..... G01N 2021/0389; G01N 2021/513; G01N 2021/0346; G01N 33/4875; G01N 2015/00; C12Q 1/04; C12Q 1/06; C12Q 1/18; C12Q 1/10; B01L 3/50; B01L 2300/04; B01L 2300/0809; B01L 3/508
See application file for complete search history.

(56) References Cited

U.S. PATENT DOCUMENTS

| | | | |
|---|---|---|---|
| 3,928,140 A | 12/1975 | Wyatt et al. | |
| 4,066,360 A | 1/1978 | Breddin et al. | |
| 4,083,638 A | 4/1978 | Sandrock | |
| 4,101,383 A | 7/1978 | Wyatt et al. | |
| 4,113,386 A | 9/1978 | Lepper, Jr. | |
| 4,119,407 A | 10/1978 | Goldstein et al. | |
| 4,577,970 A | 3/1986 | Meserol | |
| 4,754,613 A | 7/1988 | Brito | |
| 4,865,813 A * | 9/1989 | Leon ................ | B01L 3/502 210/198.1 |
| 4,895,446 A | 1/1990 | Maldari et al. | |
| 5,139,031 A | 8/1992 | Guirguis | |
| 5,187,368 A | 2/1993 | Galante et al. | |
| 5,212,667 A | 5/1993 | Tomlinson, Jr. et al. | |
| 5,351,118 A | 9/1994 | Spinell | |
| 5,506,679 A * | 4/1996 | Cooper ................ | G01N 21/53 356/338 |
| 5,525,475 A * | 6/1996 | Ladouceur ......... | G01N 33/5302 210/634 |
| 5,616,923 A | 4/1997 | Rich et al. | |
| 5,693,944 A | 12/1997 | Rich | |
| 6,048,337 A | 4/2000 | Svedman | |
| 6,230,045 B1 | 5/2001 | Hoogenraad et al. | |
| 6,333,008 B1 | 12/2001 | Leistner et al. | |
| 6,506,346 B1 * | 1/2003 | Monro .................... | B01L 3/502 422/544 |
| 6,573,992 B1 | 6/2003 | Drake | |
| 6,861,230 B1 | 3/2005 | Murphy et al. | |
| 7,430,046 B2 | 9/2008 | Jiang et al. | |
| 7,961,311 B2 | 6/2011 | Weichselbaum et al. | |
| 8,339,601 B2 | 12/2012 | Weichselbaum et al. | |
| 2001/0019406 A1 * | 9/2001 | Russell ................ | G01B 11/255 356/124 |
| 2003/0048433 A1 | 3/2003 | Desjonqueres | |
| 2004/0070756 A1 | 4/2004 | Rastopov | |
| 2004/0185552 A1 | 9/2004 | Grinner et al. | |
| 2004/0238746 A1 | 12/2004 | Dreyer et al. | |
| 2005/0148085 A1 | 7/2005 | Larsen | |
| 2005/0210996 A1 | 9/2005 | Quinn | |
| 2006/0063146 A1 | 3/2006 | Larsen et al. | |
| 2006/0065856 A1* | 3/2006 | Diaz ....................... | G01N 21/47 250/559.4 |
| 2006/0109476 A1 | 5/2006 | Werner et al. | |
| 2006/0256338 A1 | 11/2006 | Gratton et al. | |
| 2007/0155017 A1 | 7/2007 | Wyatt | |
| 2007/0159619 A1 | 7/2007 | Chu et al. | |
| 2007/0195324 A1 | 8/2007 | Adams et al. | |
| 2007/0206203 A1 | 9/2007 | Trainer | |
| 2007/0211251 A1 | 9/2007 | Weichselbaum | |
| 2008/0106737 A1 | 5/2008 | Weichselbaum et al. | |
| 2013/0089476 A1 | 4/2013 | Weichselbaum et al. | |

FOREIGN PATENT DOCUMENTS

| | | |
|---|---|---|
| EP | 1136563 | 9/2001 |
| GB | 1515681 | 6/1978 |
| GB | 2412166 | 9/2005 |
| WO | WO 00/09981 | 2/2000 |
| WO | WO 00/66763 | 11/2000 |
| WO | WO 2006/018839 | 2/2006 |

OTHER PUBLICATIONS

PCT International Search Report and Written Opinion of the International Search Authority regarding PCT/IL2006/01379, dated Jul. 11, 2008, 8 pages.

\* cited by examiner

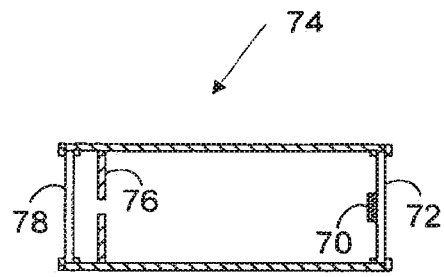
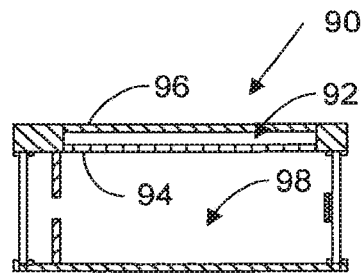
Fig. 3A          Fig. 3B
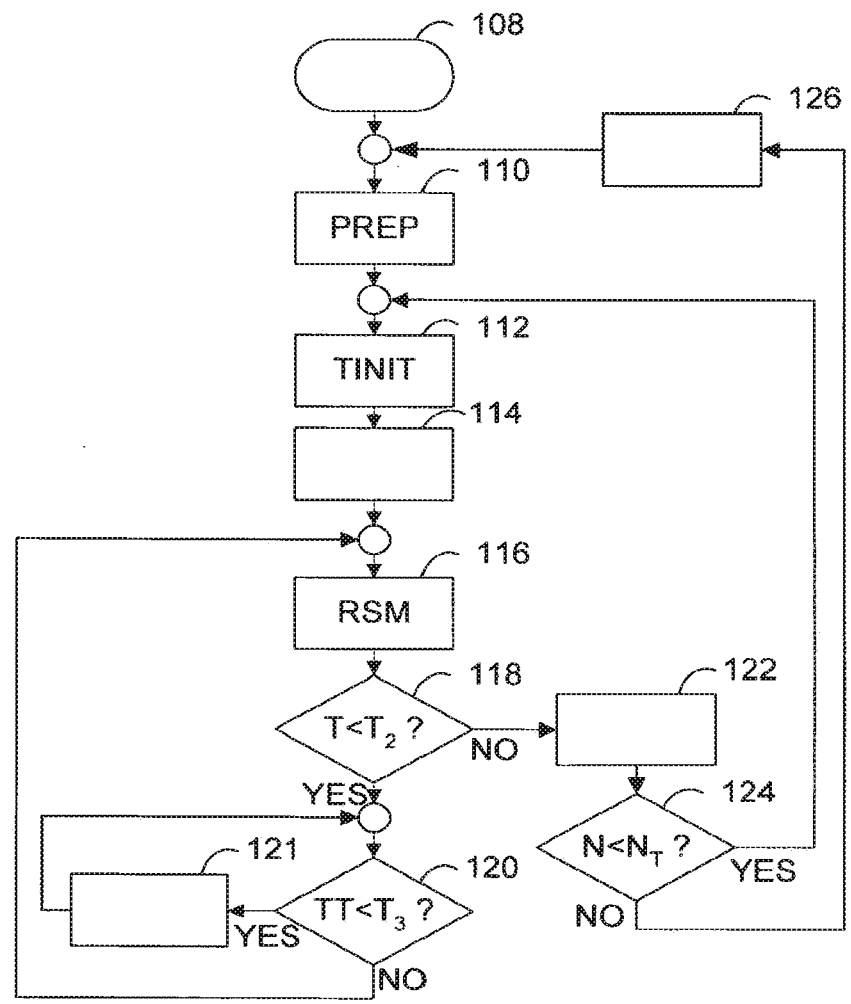
Fig. 4

METHOD OF DETECTING BACTERIA IN A FLUID USING FORWARD-SCATTER TECHNIQUE

CROSS REFERENCE TO RELATED APPLICATIONS

This application is a continuation of U.S. application Ser. No. 14/577,750, filed Dec. 19, 2014, and titled "Cuvette For Detecting Bacteria," which is a continuation of U.S. application Ser. No. 13/689,000, filed Nov. 12, 2012, and titled "Cuvette For Detecting Bacteria," which is a divisional of U.S. application Ser. No. 12/085,708, filed May 29, 2008, and titled "Counting Bacteria And Determining Their Susceptibility To Antibiotics," now issued as U.S. Pat. No. 8,339,601, which is a U.S. national stage of International Application No. PCT/IL2006/001379, filed Nov. 29, 2006, and titled "System For Counting Bacteria And Determining Their Susceptibility To Antibiotics," which claims the benefit of United Kingdom Patent Application No. (GB) 0615692.1, filed Aug. 8, 2006, and to U.S. Provisional Application No. 60/597,395, filed Nov. 29, 2005, each of which are incorporated by reference herein their entireties.

FIELD OF THE INVENTION

The present invention relates in general to assaying biological fluids. In particular the present invention relates to optically testing urine for detecting, counting bacteria and determining their susceptibility to antibiotics.

BACKGROUND OF THE INVENTION

Biological fluids such as urine, amniotic, pleural, peritoneal and spinal fluids are sometimes subjected to testing for the presence of bacteria. As a complementary step, it may be required to determine the susceptibility of such infecting bacteria to antibiotics in order to devise a treatment schedule if an infection is detected. Common analytical methods involve culturing and or microscopy, require skilled operators and are time and resource consuming. Normally, physicians and veterinarians are to wait for days in order to receive laboratory results that determine whether a human or animal subject is infected with bacteria and recommend the antibiotic most appropriate for the required treatment.

A method for determining bacterial susceptibility to antibiotic agents which is less time demanding is discussed in "Light scattering methods for antibiotic sensitivity tests", by J. Murray, P. Evans and D. W. L. Hukins, in J. Clin Pathol, (1980) 33, 995-1001. This method is based on the observation that the angle of light scattered from a sample of fluid containing bacteria changes after an adequate antibiotic agent is added to the examined fluid. Two samples of the same fluid, one of which an antibiotic agent, are simultaneously cultured. The culturing time as disclosed is significantly longer than the half-life time of the bacterial proliferation and is preferably about 90 minutes. Light scattering measurements across a wide angular range (including back scattering) are carried out for both samples by means of a differential light scattering photometer. Representative parameters, such as a displacement parameter that is proportional to the area separating between the plots of angular scattering profiles of the two samples divided by the angular range, are calculated. The values of such parameters are matched with a calibration scale for determining the susceptibility of bacteria to a specific antibiotic agent. However the results of implementing this method are not satisfactory as at least 20% of disagreement between tests attained using the disclosed method compared to a common method of incubation and microscopy are reported.

Besides the common culture methods, a number of additional techniques have been developed for the determination of the presence of bacteria in fluids, including, for example, test strips for screening for urinary tract infection (UTI), based on the testing for the presence of products within the sample created by infecting bacteria such as nitrite. However the above-mentioned method fails to detect bacteria that do not generate specific products. The method requires high bacterial concentration in the examined sample and therefore such screening process is prone to insufficient sensitivity and relatively low specificity.

International patent application WO 06018839 A2 discloses a system and a method for detecting and counting bacteria in such biological fluids. The disclosed method includes the steps of: (1) removing particles larger in size than the bacteria by filtering a sample of the fluid; (2) measuring the intensity of light scattered from the filtered fluid at one or more points displaced from the axis of the illuminating light beam; (3) associating a scattering profile with the scattering measurements; (4) comparing the associated scattering profile with stored reference scattering profiles; (5) bacterial concentration is determined by the respective count related to the reference scattering profile that fits best the associated scattering profile. The stored basic profiles according to the disclosed method consists of statistically averaged measured and or calculated scattering profiles relating to calibrated samples of filtered fluids and or linear combinations of such profiles. A cuvette especially suited for such light scattering measurement is also disclosed. Obviously such method is capable for significantly reducing the time and labor associated with detecting bacterial infection however the susceptibility of the detected bacteria to antibiotics remains unsolved.

In U.S. Pat. No. 6,861,230 a method for testing the growth characteristics of bacteria including testing bacterial susceptibility to an antibiotic agent is disclosed. This method combines culturing a sample of fluid and luminescence measurements of the cultured sample. At a preparation stage a sample of the fluid containing the antibiotic agent is cultured for a while for generating a base line level of free adenylate kinase. Bacterial susceptibility is determined by comparing levels of free adenylate kinase repeatedly measured such that: a first measurement is carried out; then the antibiotic agent is added to the examined sample, than after a delay of preferably fifteen minutes a second measurement is made. The level of adenlytate kinase increases in cases in which the bacteria are susceptible to the antibiotic agent. The disclosed method is reported to be sensitive even in cases in which the bacterial concentration in the examined fluid is considerably low and or the second measurement of the level of adenylate kinase is delayed by a time interval that is shorter than the preferred time interval. However its implementation requires wet chemistry, culturing and the use of relatively sophisticated equipment.

Therefore a rapid and labor saving screening method that can obviate a significant amount of expensive and time-consuming work in the performance of the tests is beneficial.

BRIEF DESCRIPTION OF THE DRAWINGS

FIG. 3A is a longitudinal sectional view of a cuvette providing for detecting bacteria according to a preferred embodiment of the method of the present invention;

FIG. 3B is a longitudinal sectional view of a cuvette for detecting bacteria according to another preferred embodiment of the method of the present invention;

FIG. 4 is a flowchart describing a process for detecting and counting bacteria and determining their susceptibility to antibiotics;

DETAILED DESCRIPTION OF THE PRESENT INVENTION

In accordance with the present invention, a method for counting bacteria suspended in a fluid is provided. The procedure according to the invention first employs mechanical filtering of a sample of an examined fluid followed by measuring intensities of light scattered by the filtered sample prior to and following an introduction of an antibiotic agent. The filtering provides for excluding particles whose sizes exceed the size of bacteria. The samples of fluid are taken from specimens normally received in a laboratory for screening bacteria, such as associated with hospitals and or medical clinics. The examined fluids according to the invention include but are not limited to biological fluids, such as urine, amniotic, pleural, peritoneal abdominal and spinal fluids. The received specimen, or the sample of the fluid, need not be cultured, or chemically treated prior to the test according to the method of the invention.

Figure 1:
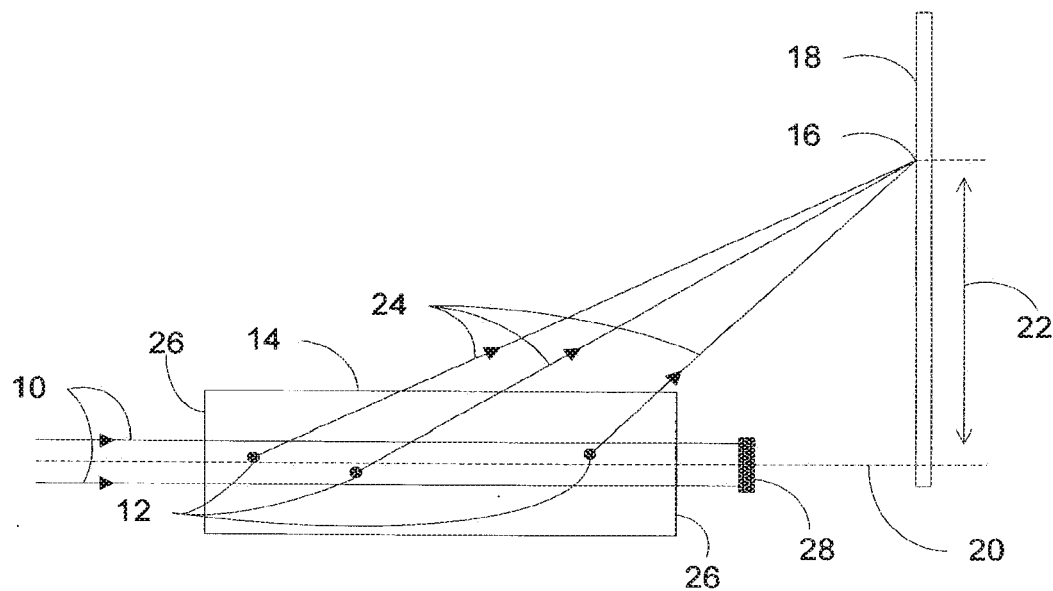
FIG. 1 is a schematic presentation of a light scattering measurement according to the present invention.

Reference is first made to FIG. 1, which schematically shows a setup for light scattering measurement according to the invention. A coherent light beam, collimated within a beam volume confined by light rays 10, illuminates particles 12 suspended in a fluid contained in cuvette 14. Point 16 located on a face of light detector 18 is placed aside from optical axis 20 by a distance indicated by double arrow 22. Light scattered by particles within a volume through which the illuminating light propagates coherently accumulates to give the intensity of light measured at point 16. Such particles are particles 12, or other particles similarly suspended in the fluid. Other possible scatterers are internal discontinuities present within, or particles located on, windows 26 and or the walls of cuvette 14. Light obscuring means 28 prevents any direct illuminating light to reach light detector 18. The scattered light generates a speckles interference pattern on the face of light detector 18, referred hereinafter by speckles image.

Dynamics of a Speckles Image

Speckles images vary in time due to Brownian motion and or bacterial motility. The mean value of the magnitude of a velocity of bacteria moving in a Brownian motion is typically in the range of a few tenths of micrometer per second (μm/s) close to 1 μm/s. A typical length of a time interval in which such bacteria "forget" their direction is about 10 seconds. Motile bacteria can swim substantially linearly at a velocity that is significantly higher and is far beyond the range of Brownian motion. The motion of motile bacteria is characteristically interrupted by quiescent periods in which the bacteria tumble and randomly change their direction of motion. Furthermore, motile chemotactic bacteria are able to move towards higher concentrations of attractants and avoid higher concentrations of repellents by sensing temporal changes in chemo-effector concentrations. (An exemplary explanation of bacteria motility and chemotaxis is given in: "Motile behavior of bacteria", H. C. Berg, Phys. Today, (January 2000), http://www.aip.org./pt/jan00/berg.html.) Motile bacteria can also move along a gradient of temperatures in what is known as thermotaxis. Therefore inducing chemotactic or thermotactic motion may impact the patterns of the speckle images thereby enhancing the sensitivity of the detection and measuring a concentration of motile bacteria suspended in fluids, as well as for determining their susceptibility to various antibiotic agents, as further described infra.

Features of the System of the Invention

Figure 2:
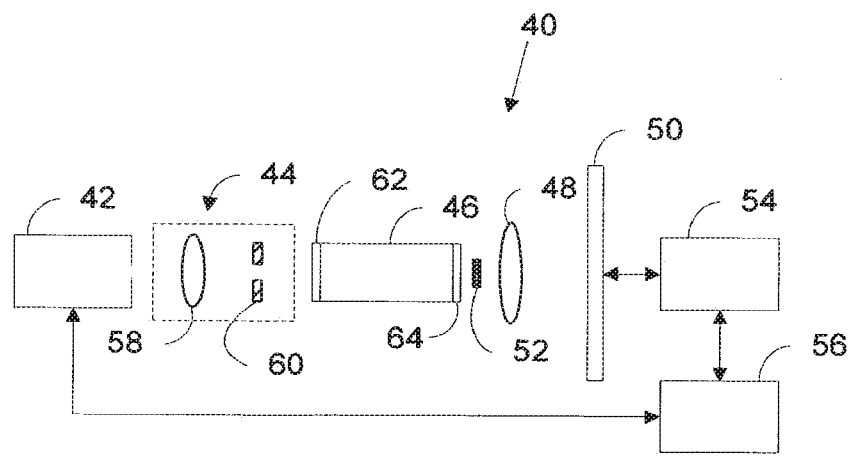
FIG. 2 is block diagram describing a system for detecting and counting bacteria according to the method of the present invention.

Reference is now made to FIG. 2 schematically showing system 40 that is suitable for counting bacteria according to the present invention. Light emitted from coherent light source 42, such as a laser source, passes through collimator 44 and the collimated beam enters cuvette 46. Light scattered by particles within cuvette 46 is focused by means of converging simple or compound lens 48 to form images across the face of light detector array 60. Light obscuring means 52 blocks the illuminating beam. Receiver unit 54 controls detector 50, receives, conditions and digitizes signals induced by the scattered light and temporarily stores them. Processing and control unit 56 provides for controlling the test process, receiving data and commands from the operator, powering light source 42 and receiver unit 54, reading the signals temporarily stored in receiver unit 54 and for carrying out signal and data processing. Results of tests and prompts to an operator are displayed on an operator display, not shown. Dedicated input keys linked to processing and control unit 56, not shown, provide for entering data and or commands to the system. Optionally processing and control unit 56 transmits data and results of tests to and receives data and commands from a remote computer. Collimator 44 consists of a simple or compound lens 58 and one or more diaphragms 60 containing an aperture.

Reference is made to FIGS. 3A and 3B showing longitudinal sectional views of a cuvette that is suitable for detecting, counting bacteria and/or determining their susceptibility to antibiotic agents according to two preferred embodiments of the method of the present invention. Light obscuring means 70 is disposed on the inner surface of window 72 of cuvette 74. Diaphragm 76 whose aperture is coaxial with obscuring means 70 is internally disposed adjacent to window 78. Cuvette 90 is especially suited for screening tests in which chemotaxis is exhibited. An obscuring means and a diaphragm having an aperture are internally disposed within cuvette 90 as is described hereinabove. Compartment 92 for containing a suitable chemo-effector that is a known attractant or a repellant agent is confined between divider 94 and sidewall 96 of cuvette 90. Divider 94 has a porous wall facing sidewall 96 and a removable cover facing lumen 98, both are not shown. The removable cover when is placed prevents any transfer of material contained in compartment 92 into lumen 98. Removing the cover off the porous wall, which is firmly attached to cuvette 90, provides for transferring the chemical reagent contained in compartment 92 and dissolving in, or mixing with, the fluid contained in lumen 98. Alternatively, regulating the temperature of one or two opposing sidewalls of cuvette 74 effects inducing a gradient of temperatures across the sample of fluids providing for a thermotactic motion.

Cuvettes such as cuvette 74 or 90 are typically mounted in association with an external housing including aligning means providing for aligning the cuvette with the optical axis of the system. Such housing has an inlet for filling compartment 92 with a suitable chemical reagent and another for filling lumen 96 or the lumen of cuvette 74 with a filtered fluid and or an antibiotic agent. Optionally a cuvette housing is provided with a filter having pores that are not smaller than the sizes of the bacteria.

The components of a cuvette that are suitable to be employed according to the invention are made of materials such as plastic resins typically utilized for manufacturing disposable containers for liquids. Such materials that are insoluble in the examined fluids, and are chemically passive to the chemical reagents and or the antibiotic agent utilized in the course of the testing. The windows are transparent in a range of wavelengths containing the wavelength, or wavelengths, of the source of light. The windows are made, for example, of plastic typically used for manufacturing optical lenses, glass or quartz. The homogeneity of the refraction index across the window, namely variations in the refraction index within the window, does not exceed 0.0001. The root mean square value of the surface roughness of the windows does not exceed 1 nanometer. Windows having an optical quality of their surfaces defined by a scratch/dig number 40/20 or lower are preferable. According to the invention, windows made of plastic or glass whose width does not exceed 0.5 millimeter is a viable example. The optical homogeneity of the bulk of the window and or its surface roughness impacts the signal to noise ratio of a measured intensity of the scattered light and in turn the sensitivity of the system.

Cuvettes such as cuvette 74 are typically employed for screening bacteria that are not motile and are referred hereinafter as cuvettes of the first type. Cuvettes having a compartment for containing repellants or attractants such as cuvette 90 are referred to hereinafter as cuvettes of the second type. Further features of the cuvettes that are suitable for scattering measurements in accordance with the invention are described in international application WO 06018839 A2 incorporated herein by reference.

Operating a System of the Invention

Normally a cuvette of the first type is employed for counting bacteria and determining bacterial susceptibility to antibiotics. Reference is now made to FIG. 4 showing a flow chart of a process of counting bacteria and determining their susceptibility to antibiotics. Such a process includes the following steps: an initialization step 108 in which the system and the test program are initialized; a preparation step 110 in which samples of the fluid are filtered and filled into the test cuvettes; a test initiation step 112 in which a test cuvette is introduced into the system and the bacteria are detected and counted; in step 114 an antibiotic agent is manually introduced into the test cuvette; in step 116 light scattering measurements are repeatedly carried out and processed; in step 118 the system checks whether the tests related to the current specimen of fluids are completed; in step 120 the system checks whether the testing of the next antibiotic agent is to be started; in step 121 the system waits for a predefined time before carrying out the following session of repeatedly receiving speckles images; in step 122 the control cuvette related to the current specimen of fluids is tested and the system checks in step 124 if there are more specimens of fluids waiting to be tested; the process is completed in step 126.

The process starts in step 108 by manually turning on the processing and control unit by which the system is activated. The operator inputs data related to the tests plan and to the specimens, such as the identity of the examined fluid, the total number of specimens and the number of antibiotic agents $N_t$ to be examined. The processing and control unit automatically initiates the test operating program and prompt the operator to provide relevant data. A queue of the antibiotic agent according to a manually updated list of antibiotic agents that are suitable to the examined fluid is stored in a memory of the processing and control unit. At the end of this program initiation process the system stands by and waits for further commands. Meanwhile the operator manually continues in a preparation (PREP) step 110 in which he performs the following activities:

(a) mechanically filtering a sample of fluid (b) respectively filling portions of the filtered fluid into a number of cuvettes. This number exceeds the number of antibiotic agents to be screened at least by one serving for control. The remaining cuvettes are the test cuvettes each of which is dedicated to one of the antibiotic agents. Optionally, such portions of the raw fluid are pressurized through a filter installed in the housing of the respective cuvettes to fill them.

In the test initiation (TINIT) step 112 a test cuvette containing a filtered fluid is manually introduced and aligned with the system. Following a manual "start" command the system automatically activates the light source (when the first test cuvette of the first specimen of fluids is examined) and initiates clocks for measuring time; and repeatedly receives for a first predefined time interval $T_1$ a number of discrete speckles images at a predefined exposure time and repetition rate, which are collectively designated hereinafter by rates $CPS_1$. Then the system prompts the operator to introduce a predefined dose of the first agent in the current queue of antibiotic agents into this examined cuvette. Meanwhile the received speckles images are automatically processed for "counting bacteria" as further described infra. The processing results are stored in a memory of the processing and control unit. Then the system automatically pauses and waits for a first "continue" command to switch to step 116. The prompted operator continues in parallel to step 114 in which he manually introduces a suitably calibrated dose of antibiotic agent into the currently examined cuvette. The operator commands the system to continue to step 116 for performing repeated scattering measurements (RSM). The system receives discrete speckles images along the same time interval $T_1$ and at the same rates $CPS_1$. By the end of this receiving cycle the system initiates another clock designated by TT, to measure the time interleaving between two successive receiving cycles. The speckles images just received are processed for determining bacterial susceptibility to antibiotics as further described infra and the results are stored accordingly. In step 118 the system compares the value of T, which is the time elapsed since the time a "start" command has been entered to a second time interval $T_2$. The time interval $T_2$ provides for estimating a significant change in the concentration level of the bacteria due to the antibiotic agent if any such change occurs. In a case in which the elapsed time T is smaller than $T_2$ the system moves to step 120 in which it compares the value of TT to the third predefined time interval $T_3$, which is the time interval separating between two successive receiving cycles. If TT is smaller than $T_3$ the program waits for a while in step 121 and further goes back to check the value of TT compared to $T_3$ in step 120. Otherwise the system goes back to step 116.

In a case that T is not smaller than $T_2$ the process continues to step 122 in which the operator is prompted to replaces the currently screened cuvette with the control cuvette. The system automatically measures the concentration of bacteria considering the control cuvette following a continue command to be entered by the operator. The respective data considering the measurements of the screened and control cuvettes are stored in the memory of the controller and the operator is further presented with the results.

In exceptional cases, such as cases in which discrepancies between the intermediate and or the final results extends beyond a predefined threshold, the operator is prompted to partially or entirely repeat the test process accordingly. At this stage the program automatically switches back to step 110, not shown, where it waits for a "start" command to be manually entered by the operator after completing the respective preparations and modifying the parameters of the system accordingly. Normally, the program continues to step 124, as shown, in which the system checks if the number N of successfully completed tests is smaller than the total number of samples of fluid NT. In a case that there are more samples waiting to be tested the system prompts the operator to proceed with preparing a new sample for screening starting at step 110. Meanwhile the system waits for a "start" command, to be manually entered by the operator when he is ready, to switch to step 112. Otherwise the system completes the processing related to the last sample of fluids and further determines the antibiotic reagent or reagents to which the bacteria detected in the respective cuvette are mostly susceptible as is further described infra. The process is completed in step 126 after the data is optionally transmitted to a remote computer.

A process for detecting and optionally counting bacteria according to a preferred embodiment of the present invention is hereby described with reference to the same FIG. 2. However all the steps 114-121 are avoided. By the end of step 112 the program automatically continues to step 122. In step 122 the system computes averaged difference plots which are further matched to a stored calibration scale as described infra. Then in step 124 the system checks whether the number of completed tests exceeds the total number $N_t$ of cuvettes to be tested. In a case of positive answer the process is completed in step 126 after the operator is displayed with the results and the data is optionally transmitted to a remote computer. Otherwise the system prompts the operator to replace the tested cuvette with the following one and switches to wait at the beginning of step 112 for a new "start" command.

Signal and Data Processing

Background signal originated by particles suspended in the sample of fluid that are larger than the bacteria are excluded by mechanically filtering according to the method of the present invention. However there are sources and light scatterers other than the bacteria that can contribute a stationary background signal. Such signals are typically originated by stationary particles present within the illuminated space, impurity of the light source, defects in, and or particles contaminating, the optical components. Therefore a difference plot is computed for excluding stationary background according to a preferred embodiment of the present invention. The intensity measured in every pixel of a speckles image is subtracted from the intensity measured in the same pixel of a preceding speckles image to form a difference plot. The difference plot is an image having the same number and arrangement of pixels as of a speckles image, whose intensities equal the absolute value of the respective differences. Therefore a difference plot displays only the time dependent components of the intensity of light scattered by the examined fluid.

A number of such difference plots are averaged in time and or in one or two-dimensional region of scattering angles to form an averaged derivative of the concentration of scatterers in time. Obviously difference plots and averaged derivatives are smoother than speckles images and the rate in which they change in time mainly depends on the rate in which the concentration of non-stationary scatterers changes. Typically the dynamic range of difference plots and averaged derivatives is smaller than the dynamic range of the respective speckles images and their signal to noise ratio is better.

For counting bacteria first a scattering profile is associated to an averaged derivative computed for the earlier speckles images received when examining a test cuvette. Such association is achieved for example by a common numerical fitting technique. Alternatively a number of the earliest speckles images received for a test cuvette are similarly averaged in time and or in one, or two, dimensional angular region. A scattering profile is associated to such averaged speckles images by employing common numerical fitting of curves or three-dimensional surfaces. The associated scattering profile is then compared to standard scattering profiles stored in the system. The concentration of bacteria in the examined fluid equals the concentration of the standard scattering profile that best fits the associated scattering profile. The set of standard scattering profiles constitutes a calibration scale to which the scattering profiles associated with the measurements are compared for estimating the bacterial concentration of the examined fluid.

For determining the susceptibility of bacteria to an antibiotic agent, an average value of at least two averaged derivatives computed first for a test cuvette, immediately following the introduction of an antibiotic agent, are compared to an average of the same number of averaged derivatives computed for speckles images received a few minutes later, preferably after more than 5 minutes. The antibiotic agent for which the difference between these averaged derivatives is the larger is determined.

A control count test includes the steps of detection of bacteria and determining their concentration. The test is carried out in consideration with the time elapsed from the examination of the first test cuvette, as is described above.

Calibrated scattering profiles are prepared according to a preferred embodiment of the present invention by statistically averaging scattering profiles measured or computed for calibrated specimens of fluids containing, and specimens free of, bacteria. Standard scattering profiles include calibrated scattering profiles and linear combinations of calibrated profiles. Calibrated scattering profiles and or standard scattering profiles are pre-stored in the system. Further features of the calibrated profiles and standard profiles as well as a more detailed description of fitting techniques are described in international patent application WO 06018839 A2.

EXAMPLE 1

A simulated analysis of speckles images was conducted. A synthetic model of urine was prepared in which 2-4 µm diameter spheres having the same dielectric constant as those of bacteria represent bacteria. The are randomly distributed in a uniform medium matching an aqueous solution of salt. Randomly distributed spheres whose radius is smaller than one micron and having a matching dielectric constant represent salt particles. The synthetic urine is contained within a cylinder having a diameter of 0.5 millimeter (mm) and a height of 55 mm. This cylinder conforms a volume separating between the aperture of diaphragm 76 and light obscuring means 70 within cuvette 74 shown in FIG. 3A to which reference is again made. The particles are coherently (spatially and temporally) illuminated such as by means of a laser diode. The intensity of scattered light measured at a point across the face of the light detector is calculated employing coherent ray tracing in which the intensity at the face of the scattering particle conforms the scattering angular distribution according to the Mie theory. [H. C. van de Hulst. "Light scattering by small particles", John Wiley & Sons publishing, NY, 1957].

Figure 5:
FIG. 5 is a simulated speckles image of a sample of synthetic urine containing bacteria.

Reference is now made to FIG. 5 showing a speckles image such calculated as received across one quadrant of a planar detector array. The intensity of the scattered light as is shown in FIG. 5 decreases with the scattering angle conformal with the scattering angular distribution according to the Mie theory. The spatial frequency of the speckles increases with the scattering angle as a larger number of particles, which are randomly distributed, contribute to the speckles interference pattern.

EXAMPLE 2

Figure 6:
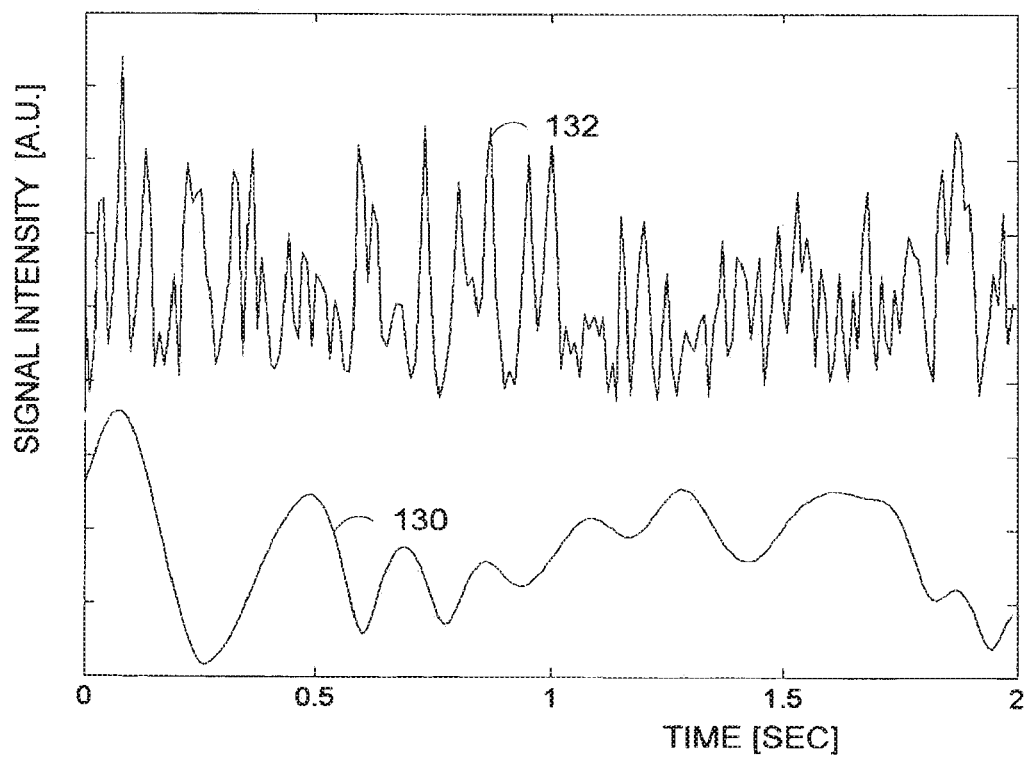
FIG. 6 shows exemplary intensity time profiles calculated for bacteria at a motion.

An analysis of the dynamics of a simulated speckles image employing the same physical models and approach as is described in example 1 hereinabove was conducted. Reference is now made to FIG. 6 showing exemplary temporal behaviours of the intensity of the scattered light calculated at a point on the face of the light detector. The point is spaced 1 mm aside from the optical axis of the system. The particles suspended in the synthetic urine are moving in uniformly distributed directions at velocities having normally distributed magnitudes. Plot 130 shows a simulated intensity-time profile in which the mean value of the magnitude of the velocities is 0.25 µm/sec. Plot 132 shows another simulated intensity-time profile in which the mean value of the magnitude of the velocities is 5 µm/sec. The signal intensity received by the light detector at this point is measured in arbitrary units (A.U.). The time is given in seconds (SEC). The scale of the signal intensity is linear and Plot 132 is shifted aside from plot 130 (for graphical purposes). Particles moving in higher speeds cause a segment of the resulted speckles image to change and flicker at a higher rate than a similar segment induced by slower particles. Whereas spatially fixed particles result a stationary speckles image.

Figure 7:
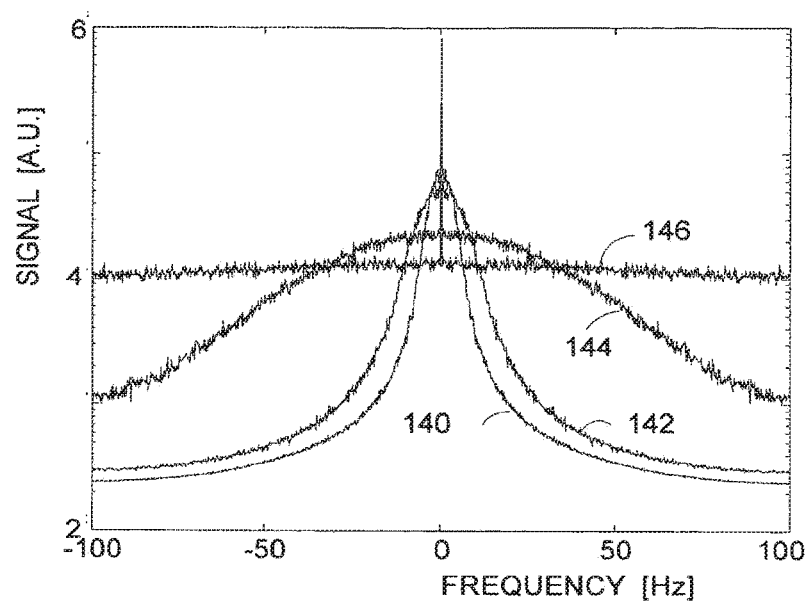
FIG. 7 is a graph presenting exemplary frequency distributions of the time dependent intensity of scattered light calculated for one pixel of a speckles image.

Reference is now made to FIG. 7 showing exemplary frequency distributions of the time dependent magnitude of a signal received at the same point as in FIG. 6. The particles move in the fluid at velocities having uniformly distributed directions and normally distributed magnitudes. Plots 140-146 show the frequency distributions corresponding to mean values of 0.25, 0.50, 2.5 and 7.5 µm/sec respectively. Frequencies are measured in Hertz (Hz) and the signal intensities measured in A.U. are plotted employing logarithmic scale. Therefore actively moving particles, such as motile bacteria whose velocities are considerably higher than velocities typically associated with Brownian motion, can be screened by a system of the invention. Furthermore, In accordance with the method of the present invention a preferable exposure time in which a speckles image is sampled in such scattering measurements is considerably smaller than a typical time cycle resulted from the frequency distribution associated with the Brownian motion.

EXAMPLE 3

An exemplary experiment displaying the features of the method and system of the invention related to the dynamics of the light scattered from fluids containing bacteria is described below. Two samples are taken from the same specimen of urine, which is free from bacteria. A calibrated quantity of *E-coli* is introduced into one of these samples, such that the bacterial concentration in the sample is $10^6$ colony-forming units per milliliter (CFU/ml). A quantity pf particles of a size of 2 µm is introduced into the other sample of urine, such that the concentration of the particles equals the bacterial concentration of the first sample. These particles are made of polymethylmethacrylate (PMMA). The two samples are mechanically filtered to exclude particles larger than 5 µm. The samples are examined with a system for detecting bacteria of the invention whose light source consists of a laser diode of 650 nanometers (nm) having a power of 0.2 milliwatt (mw) and a beam diameter of 0.5 mm. A two dimensional CMOS sensor serves as the light detector. The samples of fluids are filled into cuvettes of the first type such as cuvette 74 shown in FIG. 3A to which reference is again made. The dimensions of the illuminated volume of fluid spacing between the aperture of diaphragm 76 and light obscuring means 70 are the same as described hereinabove.

Figures 8A, 8B:
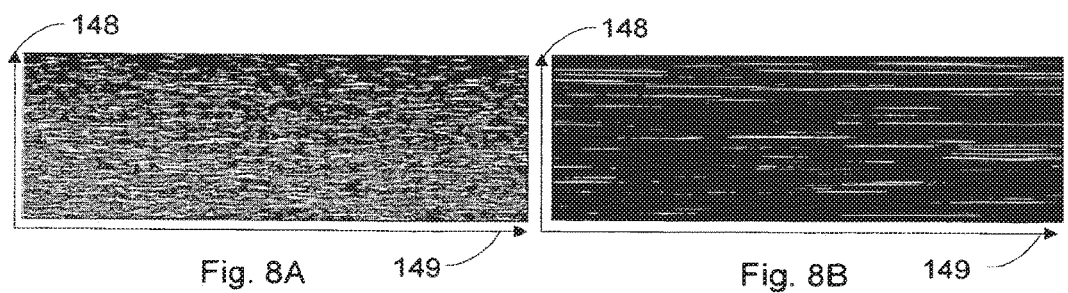
FIGS. 8A and 8B respectively show an intensity—scattering angle—time profile of a sample of urine containing E-coli and a sample of urine containing PMMA particles.
Figure 8C:
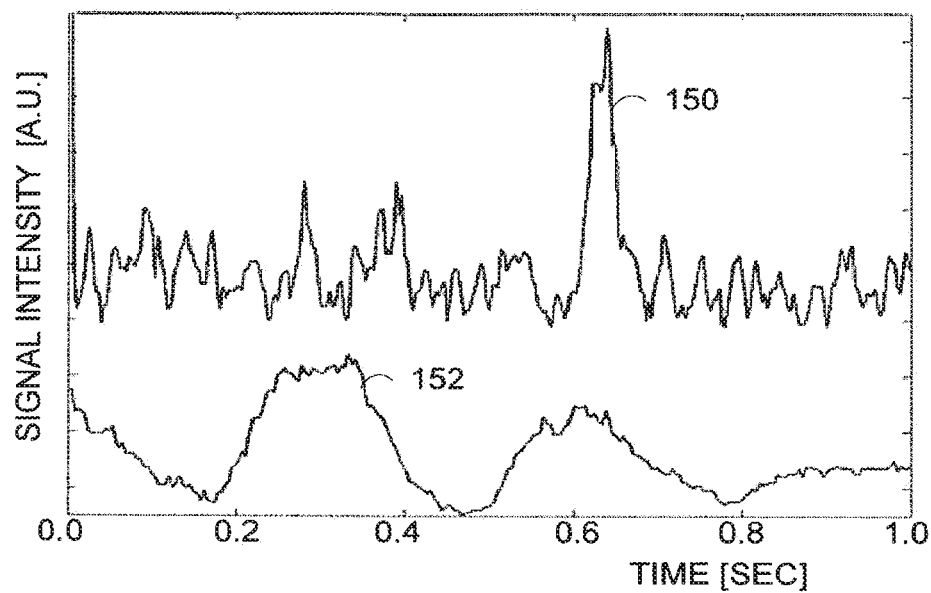
FIG. 8C shows intensity—time profiles measured at one of the pixels shown in FIG. 8A.

Reference is now made to FIGS. 8A-8C. In FIG. 8A the intensities of signals of light scattered by the sample including *E-coli* are shown. The signals received by a segment of a row of pixels disposed across the face of the light detector; are periodically sampled at a rate of 300 Hz along a time interval of one second. In FIG. 8B the intensities of signals of light scattered by the sample including PMMA particles are shown. The signal are received by the same segment of pixels and similarly sampled and plotted as in the case shown in FIG. 8A. The magnitude of the measured intensity is represented by the colour of the plots ranging from black for zero intensity to white for maximal intensity measured. Any point along a line that is parallel to axis 148 corresponds to the same point in time, whereas any line parallel to axis 149 corresponds to the same scattering angle, or the same pixel within the segment of the row of pixels.

A series of almost horizontal lines whose colour periodically changes in a moderate rate is shown in FIG. 8B. Such temporal behavior corresponds to a substantially narrow frequency distribution of the time dependent intensity of the scattered light. Such behavior is typical in cases in which the particles such as the PMMA particles move in a Brownian motion. E-coli bacteria are motile and are capable to move at significantly higher speeds. Therefore the corresponding frequency distribution is considerably broader in which higher frequencies have a considerable contribution in making FIG. 8A look noisy and spiky.

Intensity-time profiles related to these two samples are shown in FIG. 8C. The intensities of a signal received in an exemplary pixel (which is one of the pixels associated in generating FIG. 8A), are measured in arbitrary units. The intensity scale is linear and the time is measured in seconds (SEC). Plot 150 corresponds to the sample including E-coli whereas plot 152 to the sample including PMMA particles. Plot 150 is shifted aside from plot 152 (for graphical purposes). The considerably higher frequencies induced by the bacterial motility significantly contribute to the temporal behaviour of plot 150. Whereas the considerably low frequencies in the range of a few Hertz induced by the Brownian motion of the PMMA particles provide for the moderate time dependence of plot 152. Aided by such intensity plots as FIGS. 8A-8C an operator can select an exposure time and a sampling rate in which speckles images are to be received.

EXAMPLE 4

An experiment demonstrating features of a method for data processing according to a preferred embodiment of the present invention is described below. An exemplary calibrated specimen of urine containing E-coli is prepared. The system employed in this experiment is described in example 3 hereinabove. Following the procedure described in step 110 and on, shown in FIG. 4 to which reference is again made, the following activities are made. First a sample taken from this specimen is mechanically filtered to exclude particles whose sizes exceed 5 μm. Then a portion of the filtered fluid is filled into the first test cuvette, which is a cuvette of the first type. The cuvette is placed and aligned and measurements of light scattering for detecting and counting bacteria are made.

Figure 9A:
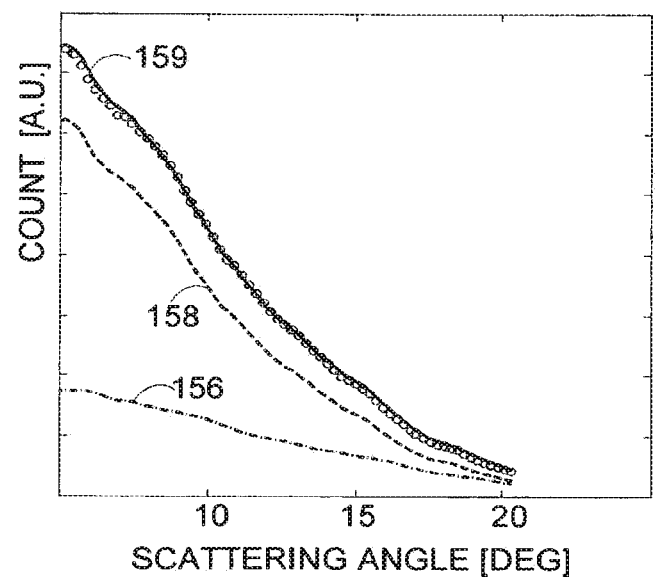
FIG. 9A respectively shows exemplary graphs of two standard scattering profiles, a scattering profile associated to measured intensities of light scattered by a sample of urine, and a fitted scattering profile, as a function of the scattering angle.
Figure 9B:
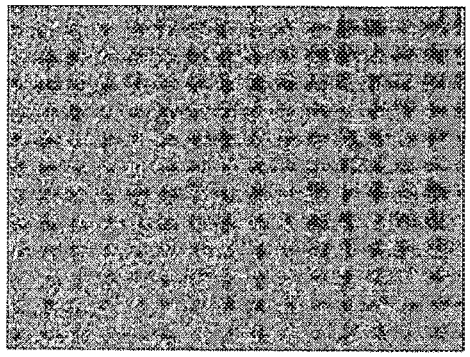
FIGS. 9B and 9C respectively show difference plots computed in two different points in time employing measurements of light scattered from an exemplary sample containing E-coli.
Figure 9C:
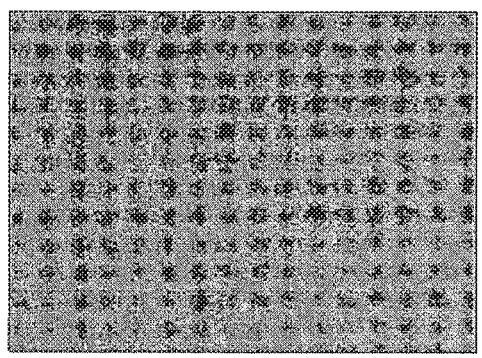

Reference is now made to FIGS. 9A-9C. In FIG. 9A two exemplary calibrated scattering profiles of a set of calibrated profiles and the measured and fitted scattering profiles of this urine sample are respectively shown. Curve 156 represents the calibrated scattering profile of uninfected urine. Curve 158 represents one of the calibrated scattering profiles of urine containing bacteria at a specific bacterial concentration level. Curve 159 represents the scattering profile fitted to the examined sample. The circles represent values of the associated scattering profile as measured. The continuous line represents the best-fitted linear combination of calibrated scattering profiles representing urine containing bacteria at a concentration of $10^5$ CFU/ml. A considerably high level of matching is demonstrated over a significant range of scattering angles. The detected level of bacterial concentration in this examined sample deviated from the reference level by a few percent.

Figure 9D:
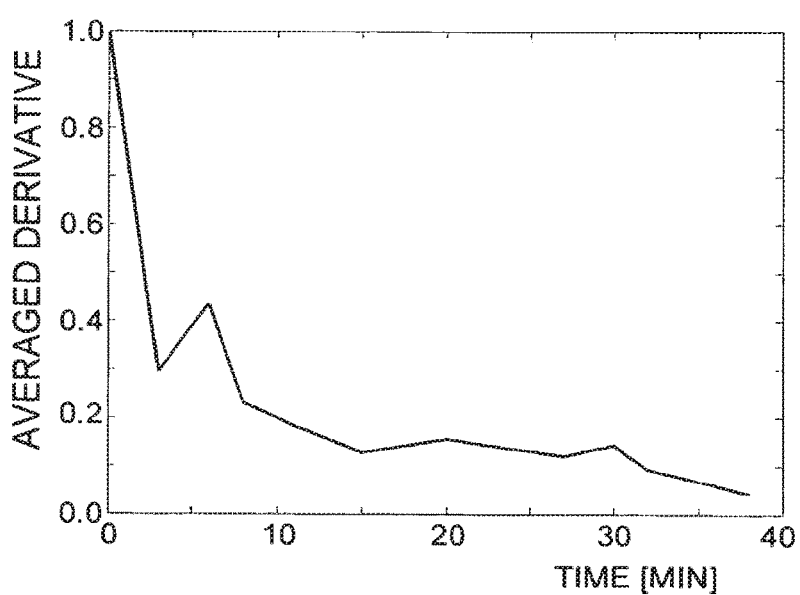
FIG. 9D shows a time profile of an exemplary average derivative of the concentration of scatterers in time, computed for an exemplary sample containing E-coli.

At this stage a calibrated dose of gentamicin is such introduced that its concentration in the test cuvette equals 1%. In FIGS. 9B and 9C two difference plots computed following the introduction of the antibiotic agent into this test cuvette are respectively shown. Two speckles images successively received at two different points in time separated by at least 20 milliseconds (ms) are employed for each difference plot. The difference plots are computed by subtracting the first of each pair of these speckles images from the second one. In FIG. 9B a difference plot derived immediately following the introduction of the antibiotics is shown, whereas FIG. 9C shows a difference plot derived 30 minutes later. Although the signal levels in both difference plots is relatively low, speckles are clearly seen in FIG. 9B whereas FIG. 9C shows a considerably smoother level. A significant reduction in the concentration of non-stationary scatterers has occurred as a result of the introduction of an adequate antibiotic agent. Difference plots are averaged in time along a pre-specified time interval and or in the scattering angles across a pre-specified one, or two, dimensional angular range according to the present invention, to give an average derivative of the concentration of scatterers in time. The temporal behaviour of the average derivative associated with this sample containing E-coli is shown by reference to FIG. 9D. In FIG. 9D values of the averaged derivative normalised by their maximal value plotted versus time measured in minutes (MIN) are shown. A significant reduction (of a few tens of percents) in the values of the averaged derivative is demonstrated a few minutes after the introduction of the antibiotics.

EXAMPLE 5

An analysis of the contribution of chemotaxis and or thermotaxis to the dynamics of a simulated speckles image was conducted. The same models and physical approach as described in example 1 hereinabove were employed. The light detector modelled is a two dimensional CMOS sensor. The Brownian motion is modelled by particles' velocities having uniformly distributed directions and normally distributed magnitudes with a mean value of 0.5 μm/sec. Chemotactic or thermotactic motions are modelled by a uniform particles' velocity of 5 μm/sec perpendicular to the laser beam.

Figure 10A:
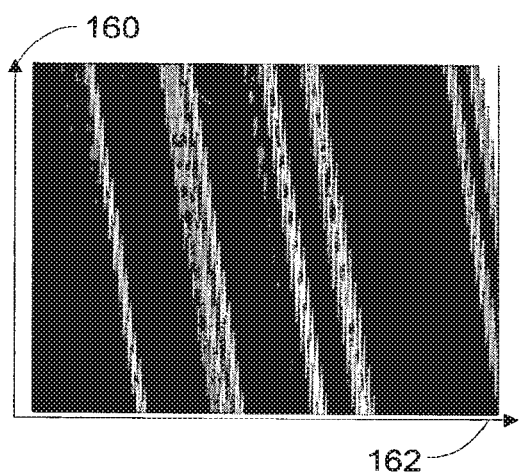
FIGS. 10A and 10B respectively show simulated intensity—scattering angle—time profiles induced by particles having constant unidirectional velocity and by particles having the same unidirectional velocity that are simultaneously moving in a Brownian motion.
Figure 10B:
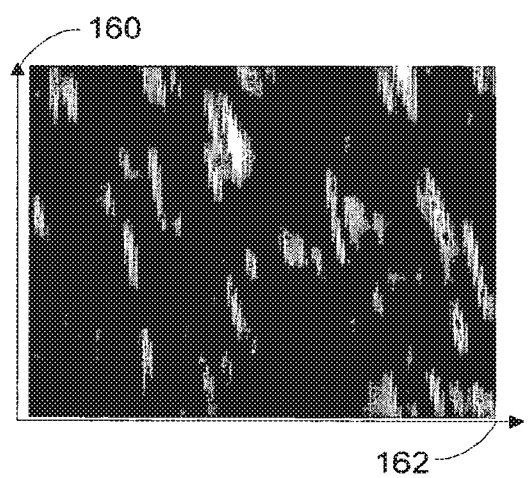

Reference is now made to FIGS. 10A-10B. In FIG. 10A a three dimensional intensity—scattering angle—time profile of particles moving in the same direction measured along a segment of a row of pixels is shown. The intensity of the scattered light measured in each pixel is represented by a scale of black and white colours; in which black represents zero intensity and white represents the maximal intensity measured. The exposure time is lower than 10 milliseconds and the sampling repetition rate is 100 Hz. The length of the segment of the row of pixels employed for simulating these profiles is 0.15 mm. The length of the time interval along which the simulated intensities are shown is 2 sec. Intensities shown along a line that is parallel to axis 160 are measured at the same pixel. The intensities along a line parallel to axis 162 are measured at the same point in time.

In FIG. 10B an intensity—scattering angle—time profile induced by particles moving in a Brownian motion and also having the same constant velocity component of 5 μm/sec. An averaged component of a unidirectional collective motion that exceeds 2 μm/sec is distinguishable and is different from velocities typically associated with the Brownian motion. Therefore such analysis of speckles images can also be used for studying the dynamics of bacteria by means of a system of the invention. However it is clearly demonstrated that by inducing chemotactic or thermotactic motion the sensitivity of for detecting and further measuring the concentration of motile bacteria suspended in the examined fluid, as well as for determining their susceptibility to antibiotic agents is considerably enhanced. By suitably selecting exposure times and repetition rates for receiving the speckle images in such cases, the patterns of the difference plots as well as patterns of the respective average derivatives of concentration of scatterers over time are more distinct. Therefore by employing suitably selected repetition rates and exposure times the signal to noise ratios in which the intensity of scattered light is measured are considerably improved.

The invention claimed is:

1. A method of detecting bacteria suspended in a biological fluid in a system having a light source for generating an input light beam that transmits along an input beam axis entering a cuvette to illuminate a portion of the biological fluid in the cuvette, the system further having a light detector for receiving light forwardly scattered from the biological fluid, the method comprising:
 filtering the biological fluid and placing the filtered biological fluid in the cuvette that holds the filtered biological fluid, the cuvette having a first window and an opposing second window that are transparent and made of a plastic material, the first window being located on the opposite side of the cuvette from the second window, each of the windows having an optical quality defined by a scratch/dig number that is 40/20 or lower;
 aligning the cuvette in the system such that the first window and the opposing second window are aligned with the input beam axis of the input light beam;
 regulating the temperature of the cuvette to affect the bacteria within the filtered biological fluid;
 illuminating a portion of the filtered biological fluid with the input light beam to create forward-scattered light exiting the second window in locations spaced apart from the input beam axis;
 obscuring a remaining portion of input light beam that exits the second window of the cuvette prior to the remaining portion of the input light beam encountering the light detector, the light detector being located behind the second window in the direction of the input beam axis and being spaced away from the second window in the direction of the input beam axis;
 repeatedly receiving forward-scattered signals at the light detector due to the forward-scattered light, the forward-scattered light being indicative of the bacteria within the fluid sample; and
 using the forward-scattered signals to determine a change in bacterial count over a period of time.

2. The method of claim 1, wherein the using the forward-scattered signals includes matching the forward-scattered signals with a calibration scale.

3. The method of claim 1, wherein the regulating the temperature includes inducing a temperature gradient in the biological sample.

4. The method of claim 1, wherein the using the forward-scattered signals includes measuring the intensity of forward scatted signals.

5. The method of claim 1, wherein the filtering of the biological fluid and placing the filtered biological fluid in the one cuvette includes:
 placing the filtered biological fluid in a plurality of cuvettes, wherein some of the plurality of cuvettes include different chemo-effector agents.

6. The method of claim 5, wherein the biological fluid is urine.

7. The method of claim 5, wherein the using the forward-scattered signals indicates an estimation of a change in concentration level of the bacteria.

8. The method of claim 7, wherein the change in concentration level of the bacteria indicates the bacterial susceptibility to one or more of the different chemo-effector agents.

9. The method of claim 5, further including manually placing the different chemo-effector agents into the cuvettes.

10. The method of claim 5, wherein one of the plurality of cuvettes includes a control of the biological fluid.

11. A method of detecting bacteria suspended in a biological fluid in a system having a light source for generating an input light beam entering a cuvette along an input beam axis to illuminate a portion of the biological fluid in the cuvette, the system further including a light detector for receiving light forwardly scattered from the biological fluid, the method comprising:
 filtering the biological fluid and placing the filtered biological fluid in the cuvette that holds the filtered biological fluid, the cuvette having first and second windows that are transparent and being made of a plastic material, the first window being located on the opposite side of the at least one cuvette from the second window;
 aligning the at least one cuvette in the system such that the first window and the second window are aligned with the input beam axis of the input light beam;
 regulating the temperature of the at least one cuvette to affect the bacteria within the filtered biological fluid;
 illuminating a portion of the filtered biological fluid with the input light beam to create forward-scattered light exiting the second window in locations spaced apart from the input beam axis;
 at a location behind the second window and in front of the light detector in the direction of the input beam axis, obscuring the remaining portion of the input light beam after the input light beam has exited the second window to inhibit an effect of the input light beam on the light detector; and
 repeatedly receiving forward-scattered signals at the light detector due to the forward-scattered light, the forward scatter signals being used to determine a change in a bacterial count in the biological fluid.

12. The method of claim 11, wherein each of the windows has an optical quality defined by a scratch/dig number that is 40/20 or lower.

13. The method of claim 11, wherein the filtering of the biological fluid and placing the filtered biological fluid in the one cuvette includes:
 placing the filtered biological fluid in a plurality of cuvettes, wherein some of the plurality of cuvettes include different chemo-effector agents.

14. The method of claim 13, further including determining bacterial susceptibility to the different chemo-effector agents based on the forward-scattered signals.

* * * * *